(12) United States Patent
De Haan (10) Patent No.: US 7,521,247 B2
(45) Date of Patent: Apr. 21, 2009

(54) CARTRIDGE FOR MONITORING THE FUNCTION OF A DEVICE FOR TESTING BLOOD PLATELET FUNCTION, METHOD FOR FUNCTION MONITORING, AND USE OF A TEST FLUID

(75) Inventor: Jacob De Haan, Homberg/Ohm (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 849 days.

(21) Appl. No.: 11/017,945

(22) Filed: Dec. 22, 2004

(65) Prior Publication Data
US 2005/0136541 A1 Jun. 23, 2005

(30) Foreign Application Priority Data
Dec. 23, 2003 (DE) ................. 103 60 814

(51) Int. Cl.
*G01N 33/86* (2006.01)
(52) U.S. Cl. ............................ 436/69; 436/63; 436/180; 422/68.1; 422/73; 422/100; 422/102
(58) Field of Classification Search ............ 436/63, 436/69, 174, 180; 422/68.1, 73, 100, 102, 422/104; 435/13; 73/64.41; 600/369
See application file for complete search history.

(56) References Cited

U.S. PATENT DOCUMENTS

| | | | |
|---|---|---|---|
| 4,604,894 A | 8/1986 | Kratzer et al. | |
| 4,780,418 A | 10/1988 | Kratzer | |
| 4,858,127 A | 8/1989 | Kron et al. | |
| 5,051,239 A | 9/1991 | von der Goltz | |
| 5,602,037 A | 2/1997 | Ostgaard et al. | |
| 5,888,826 A * | 3/1999 | Ostgaard et al. | 436/69 |
| 5,925,319 A | 7/1999 | Baugh et al. | |
| 2002/0042701 A1* | 4/2002 | Dancu et al. | 703/9 |
| 2003/0153084 A1* | 8/2003 | Zheng et al. | 436/8 |
| 2004/0224416 A1* | 11/2004 | Ghai et al. | 436/8 |

FOREIGN PATENT DOCUMENTS

| | | |
|---|---|---|
| EP | 0 716 744 B1 | 11/2001 |
| EP | 0 716 745 B1 | 11/2001 |
| WO | WO 96/00899 A1 | 1/1996 |

\* cited by examiner

*Primary Examiner*—Maureen M Wallenhorst
(74) *Attorney, Agent, or Firm*—Finnegan, Henderson, Farabow, Garrett & Dunner, L.L.P.

(57) ABSTRACT

A cartridge for monitoring the function of a device for blood platelet diagnosis has a housing which includes a test chamber and a holding chamber. A fluid volume of a test fluid is present inside the holding chamber. An air cushion is arranged above the fluid volume. A measurement cell, which has a capillary tube, is fitted in the upper part of the test chamber.

39 Claims, 5 Drawing Sheets

CARTRIDGE FOR MONITORING THE FUNCTION OF A DEVICE FOR TESTING BLOOD PLATELET FUNCTION, METHOD FOR FUNCTION MONITORING, AND USE OF A TEST FLUID

The invention relates to a cartridge for monitoring the function of a device for testing blood platelet function, with a housing which includes a test chamber and a holding chamber, and to a method for monitoring the function of such a device, and to the use of a test fluid in the device.

In a device for automated testing of blood platelet function, test cartridges are used which contain bioactive porous separating elements. The device is used to carry out tests or investigations of the blood clotting process based on the blood platelet function, with some or all of the steps in a test taking place automatically.

Hemostasis, or arrest of bleeding, involves the interaction of two biochemical systems which are controlled by different protein factors and cellular components, e.g. blood platelets. Based on current knowledge, the processes by which blood coagulates involve a multistage cascade of activations of protein factors, which cumulate in fibrin formation. Various tests have been developed to test the individual stages of this cascade and thus be able to determine whether the blood from a patient can clot satisfactorily or whether there is disturbed coagulation caused by a deficiency in one or more of the factors needed for blood clotting. It is known that the state of the blood platelets or the blood platelet function gives an indication of the ability of the blood to clot satisfactorily.

The test for investigating platelet function or primary hemostasis in human whole blood is known as the bleeding time test. The bleeding time test, which has been used for several decades, involves making a cut in the patient's forearm. To avoid such a cut, a further test was therefore developed, which can provide a much more exact blood platelet diagnosis.

U.S. Pat. Nos. 4,604,804, 4,780,417 and 5,051,239 disclose an assay system which can be used to carry out an in vitro test with blood, which can be correlated precisely and in a-reproducible manner with the in vivo bleeding time test mentioned above. The Thrombostat™ 4000 appliance is one such system. The blood platelet function is evaluated in this system by means of anticoagulated whole blood samples being sucked at a constant underpressure through a small opening located in the center of a separating wall which can be porous or nonporous. In systems in which the separating wall is porous, it is wetted, before the start of the assay, with an activator which activates the coagulation of the blood platelets. A thrombocyte plug forms at the opening, and the time needed to stop the flow of blood is measured. This time is then correlated with the blood platelet function.

The device used with the Thrombostat™ 4000 consists of three separate parts: a reagent/test chamber, a capillary, and a well for the sample. A porous separating wall containing collagen is situated in the reagent/test chamber. The reagent/test chamber must be stored in a hermetically sealed package, separate from the capillary and the sample well, in order to maintain the stability of the collagen during the indicated storage time. The capillary and the reagent/test chamber have to be manually assembled by the operator at the start of each test conducted. Moreover, the sample to be tested has to be pipetted into the sample well and incubated before the sample well can be assembled with the capillary and the reagent/test chamber. In addition, the time for the incubation step is manually set by the operator. The separate incubation step requires additional handling after the incubation time when the operator fits the assembled capillary and reagent/test chamber manually into the sample well and initiates the test sequence. At the end of the test, the expensive capillary is reused, and considerable time therefore has to be spent cleaning it.

To avoid these disadvantages, EP 0 716 745 B1 discloses a cartridge in which the user no longer has to intervene during the test cycle. This test cartridge requires no complicated sample handling mechanisms, it renders superfluous any separate external hermetic packaging for the reagent/test chambers during transport and storage, and it is intended for one-off use. The test cartridge is generally suitable for assay systems in which certain components/reagents are held separately or are combined with one another only at a suitable time.

The complex processes in primary hemostasis lead to thrombocyte adhesion and aggregation and thus to plug formation. Known appliances measure the time necessary for this under standardized conditions. The result of the time measurement is what is called the closure time, which is given in seconds. This is a measure of the platelet hemostasis capacity.

In the test, plasmatic and cellular components of primary hemostasis are recorded. This is done by in vitro stimulation of the physiological conditions leading to adhesion, activation and aggregation of the thrombocytes.

In the devices for platelet function diagnosis, a buffered sodium citrate whole blood sample is allowed to flow through a membrane opening coated with collagen (Col) or with a further activator such as epinephrine (Epi) or adenosine 5'-diphosphate (ADP), to simulate the conditions which prevail in a blood vessel. The platelets react in the presence of the plasmatic components, for example von Willebrand factor, under pressure and shearing force conditions corresponding to those of a small damaged blood vessel. Adhesion and aggregation of the thrombocytes leads to closure of the membrane opening. The time measured from the start of the measurement to when the membrane opening closes is the aforementioned closure time. Taking into consideration the overlapping closure times of normal and abnormal populations, the decision criteria in clinical studies in the PFA-100® system are based on the following reference ranges:

| Measurement cell of the device | 3.8% buffered citrate blood reference range (s) | 3.2% buffered citrate blood reference range (s) |
| --- | --- | --- |
| Collagen/Epinephrine | 94-193 | 82-150 |
| Collagen/ADP | 71-118 | 62-100 |

With the known devices for platelet function diagnosis, there is therefore a simple screening possibility available for at-risk patients with congenital thrombocyte function disorder. The measurement cells or test cartridges of these devices permit differentiation between normal and abnormal platelet function (Col/Epi) and detection of an acetylsalicylic acid-induced disturbance (Col/ADP). By means of platelet function diagnosis, very many patients with congenital thrombocyte function disorders can be diagnosed without the need for further special diagnostics, such as aggregometry. On intake of acetylsalicylic acid, there is a very rapid rise and then fall in the concentration of medicament in the serum. The consequence of this is an increase in the Col/Epi closure times, which are prolonged for days. The extent of prolongation of the closure time has been shown to differ in individual patients.

EP 0 716 744 B1 and 0 716 745 B1 disclose devices for blood platelet diagnosis, in which measurement cells or test cartridges are fitted, and describe in detail the assays for testing the blood platelet function. The assays for testing platelet function described in U.S. Pat. Nos. 4,604,804, 4,780,418 and 5,051,239 include an incubation step in the device during which the blood sample to be analyzed and the components of the assay are heated to a defined temperature, the sample and the assay components being kept separate during this incubation step. After the incubation step, a capillary tube comes into contact with the blood, and an underpressure is generated in the test chamber, which has the effect of suctioning the blood through the capillary tube. The effect of the underpressure is that the blood sample flows from a holding chamber, through the capillary tube and into a receiving chamber and through an opening in the separating element. In the case of test cartridges for use in the platelet function assay, reagents on the separating element activate the formation of a thrombocyte plug which blocks the opening, so that the blood sample can no longer flow through the capillary tube. The time needed to interrupt the flow of blood is compared with the time needed for interrupting the blood flow when the platelet function of the blood is normal. The normal range of closure time is determined by analysis or tests of normal blood.

The porous separating elements used in the known devices in the test cartridges are suitable for whole blood and blood plasma coagulation assays which are similar to the prothrombin time tests and the partial thromboplastin time tests for assessing clotting functions. The plug formation is initiated by the blood coming into contact with suitable activators for exogenous or endogenous activation. The activators are incorporated in the porous separating elements. The time needed for stopping the blood flow is for example correlated with the prothrombin time or the partial thromboplastin time of the persons to be tested.

The concentration of the substance or substances in the porous separating elements is chosen so that a closure time is obtained which reveals a difference between normal and abnormal clotting parameters. In the platelet function test, adenosine 5'-diphosphate (ADP) is a preferred reagent for incorporation in the porous separating elements. The closure time in the case of a normal blood sample depends partially on the concentration of the bioactive substance incorporated in the membrane. The concentration of this substance is chosen so that a clear difference between normal and abnormal coagulation parameters is obtained. The reagent concentration can be optimized taking into account the desired sensitivity of the assay. It is desirable that the concentration of ADP is sufficient to be able to demonstrate a slight thrombocyte dysfunction, but not so low that variable results are obtained.

In the known devices for blood platelet diagnosis, one problem is that of checking and monitoring the technical functionality of the system before the start of an assay.

This monitoring of the function of the devices differs entirely from the self-testing of the devices in which, for example, the operating voltage, current uptake, operating temperature, heating time for the sample, and similar, are checked.

The object of the invention is to check the technical functions of a device for blood platelet diagnosis.

This object is achieved by the subjects and method described in the claims, in particular by a device of the type mentioned at the outset, in which a separating element closes off in an airtight manner a fluid volume and an air cushion situated above the latter in the holding chamber, a measurement cell can be fitted into the upper part of the test chamber, and a capillary tube connects the measurement cell to the fluid volume.

In one embodiment of the device, the holding chamber can be closed off in an airtight manner by an upper closure element. The measurement cell expediently sits in an airtight manner on a peripheral base arranged on the inner wall of the test chamber. A suction device can be connected sealingly to the measurement cell and generates an underpressure in the measurement cell.

In a preferred embodiment of the invention, the test fluid contains a mixture of glycerol and water. However, other fluids or mixtures of these can be used as test fluid according to the invention, and, depending on the particular purpose, these have a comparable, i.e., within the normal fluctuation range, an identical, a lower or a higher viscosity compared to the viscosity of the sample to be tested, e.g. whole blood, platelet-rich blood plasma, blood plasma. Fluids suitable as test fluid are, for example, water, glycerol, oils, polyethylene glycol and mixtures of these. The test fluid can also contain further components which for example increase the stability and/or storage life of the test fluid or can change its viscosity, for example buffer substances, salts, antimicrobial substances, nucleic acid chains, carbohydrate chains, proteins, etc. The viscosity of the sample to be tested and of the test fluid can be determined, for example, by conventional viscosimeters.

A particularly preferred method according to the invention for monitoring the function of a device for testing blood platelet function comprises the following steps:

(1) introduce a specific volume of a test fluid in a holding chamber;
(2) closing off the fluid volume, and an air cushion located above this, in an airtight manner by means of a separating element;
(3) closing off the test chamber in an airtight manner by means of a sealing element and introducing a measurement cell into the test chamber;
(4) moving a capillary tube, connected to a measurement cell, inside the test chamber in the direction of the separating element and piercing the separating element with the capillary tube so that the latter comes into contact with the test fluid or plunges into the test fluid;
(5) generating a sufficient underpressure in the measurement cell so that test fluid flows through the capillary tube into the measurement cell;
(6) measuring the time needed until the flow of the test fluid into the measurement cell stops; and
(7) correlating the time measured in step (f) with a predetermined reference value.

The predetermined reference value in step g) is, for example, the time for the blood flow in a predetermined normal range of the device for testing blood platelet function.

The further details of the method are set out in the method measures in claims 17 through 23.

The invention makes it possible, using a test fluid, to simulate a test for determining the closure time of a normal whole blood or plasma sample by defining an initial flow speed and a suctioned total volume of the whole blood sample.

As the closure time to be expected is known, any large deviation of the closure time of the test fluid indicates that the device is not ready for use for the desired diagnosis, for example blood platelet diagnosis. Thus, for example, a leak between the suction device and the measurement cell of the device can lead to longer closure times of the test fluid.

The measurement principle for the closure time of the test fluid is that the time from the start of flow of the test fluid to when the flow stops, caused by the pressure balance between the underpressure in the holding chamber and the suction pressure in the measurement cell, is measured in time units, for example seconds.

The reproducibility of the closure time is very good, and the deviations in the parameters of suctioned total volume of test fluid and initial flow speed are very low at 1 to 2%.

Particular embodiments of the invention are explained in more detail below on the basis of illustrative embodiments shown in the drawing, in which.

The cartridge according to the invention for functional monitoring is explained on the basis of illustrative embodiments which are used in devices for blood platelet diagnosis. The outer shape and the dimensions of the housing of such a cartridge therefore correspond to the test cartridges as disclosed and described in European Patent EP 0 716 744 B1 and 0 716 745.

Figure 1:
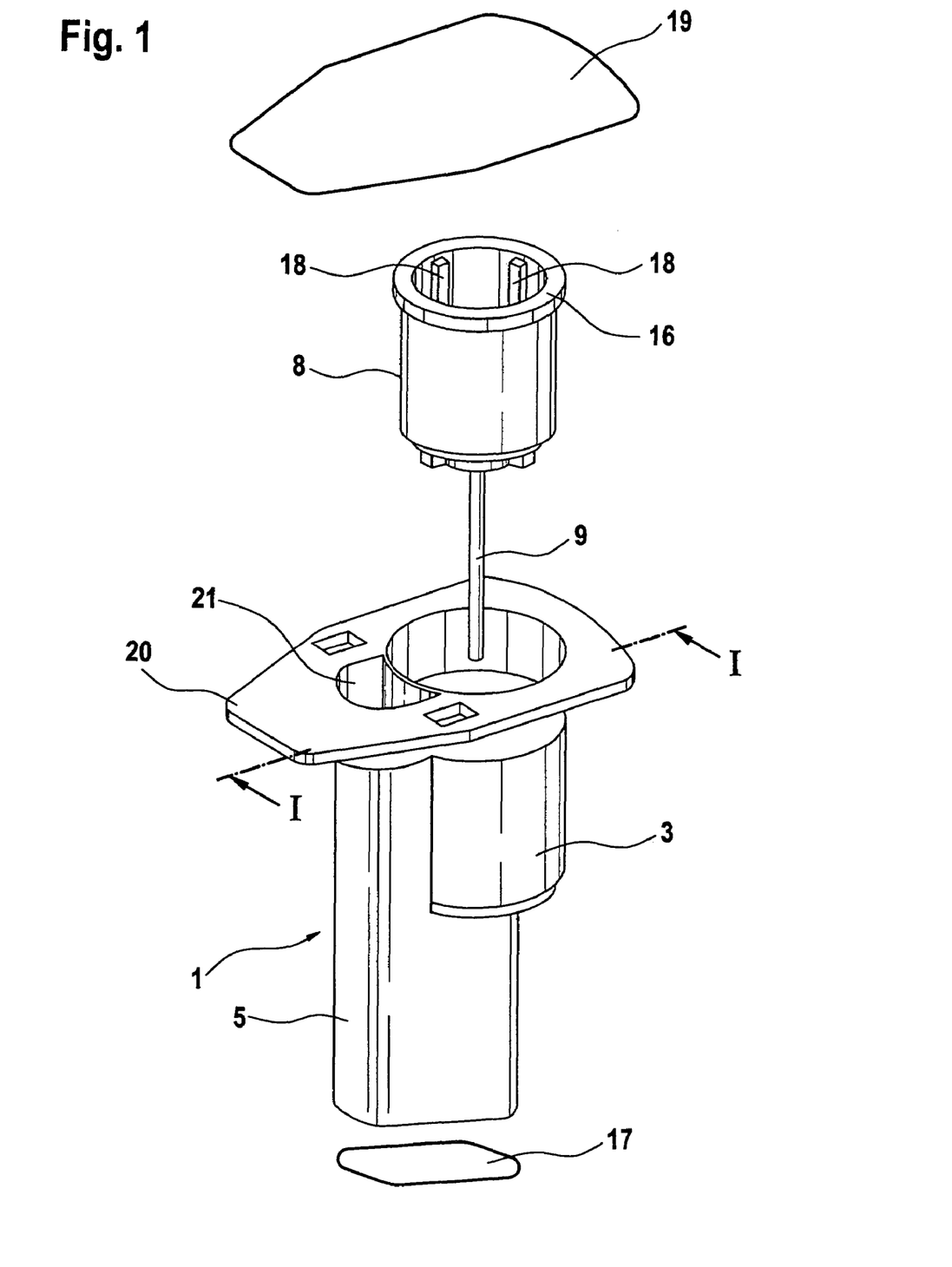
FIG. 1 is an exploded view showing a cartridge for monitoring the function of a device for blood platelet diagnosis in accordance with the invention.

FIG. 1 is an exploded view showing an embodiment of the cartridge having a housing 1 which includes a holding chamber 5 and a test chamber 3 arranged laterally on the holding chamber. On the top face of the housing 1 there is a peripheral flange 20 which extends beyond the holding chamber 5 and the test chamber 3. The geometry of the housing 1 is chosen such that the probability of inclusion of an air bubble in the cartridge is minimized. For this purpose, use is made, inter alia, of an inclined bottom 17 (see FIGS. 2 and 3) of the holding chamber 5 so as to keep air inclusion small when test fluid is introduced into the holding chamber 5 through an opening 21. By virtue of the geometry of the housing 1, the greatest possible surface contact of the test fluid with the heated housing wall is achieved, while at the same time the surface of the test fluid exposed to the air is minimized. A measurement cell 8, to which a capillary tube 9 is secured, can be fitted into the test chamber 3. On the inside of the measurement cell 8 there are blocking ribs 18 for positioning a suction attachment 13 of a suction device 12 (see FIGS. 2 and 3). A total of four such blocking ribs 18 are provided, of which two are shown in FIG. 1 and three in FIG. 2. After the measurement cell 8 has been fitted into the test chamber 3 and the test fluid has been introduced through the opening 21, the housing 1 is closed off with a removable upper closure element 19 which closes flush with the flange 20. The upper closure element 19 can be pulled off the housing 1 and removed completely from the flange 20.

The measurement cell 8 has a peripheral upper edge 16.

Figure 2:
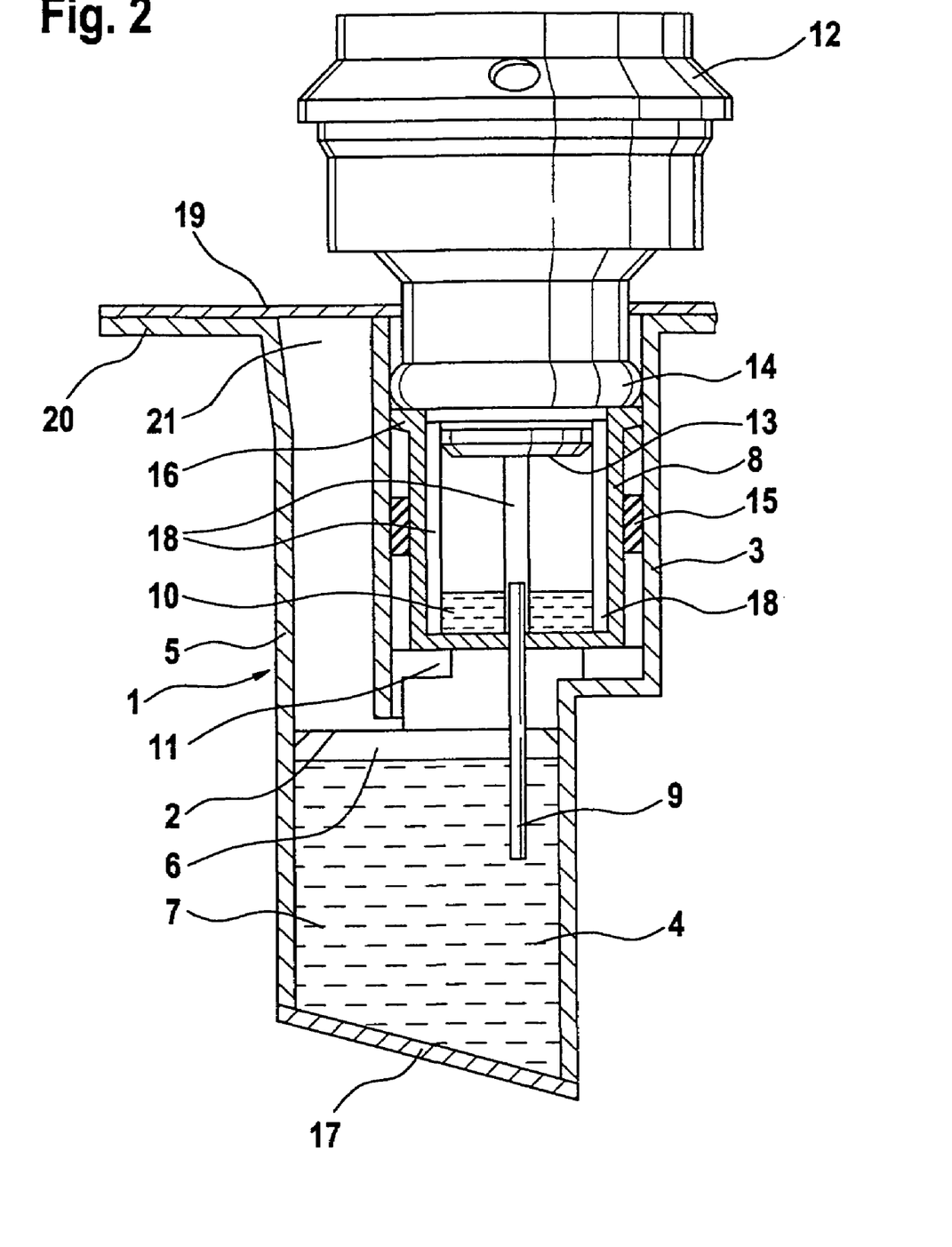
FIG. 2 is a sectional view of a first embodiment of the cartridge along line I-I of FIG. 1, in contact with a suction attachment of a suction device.
Figure 3:
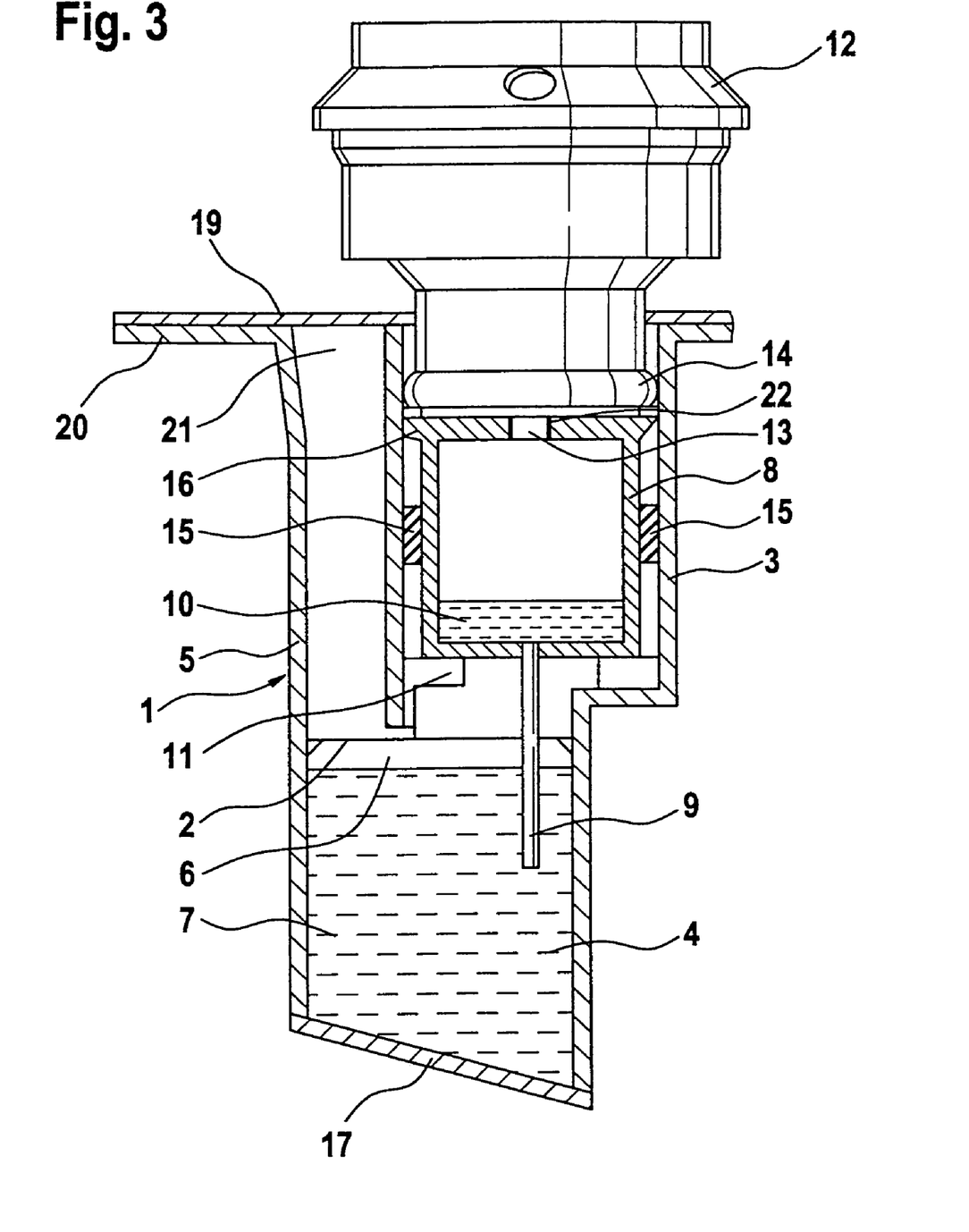
FIG. 3 is a sectional view of a second embodiment of the cartridge along the line I-I of FIG. 1, in contact with a suction attachment of a suction device.

FIGS. 2 and 3 show sectional views along line I-I of FIG. 1.

The sectional view in FIG. 2 shows a first embodiment of the cartridge in which the capillary tube 9 protrudes into the inside of the measurement cell 8. The cartridge contains, in the holding chamber 5, a fluid volume 7. The fluid volume 7 is built up by the test fluid 4 that is introduced. As soon as this has happened, the holding chamber 5 is closed off by a separating element 2, specifically at a height such that an air cushion 6 is located above the level of the test fluid 4.

FIG. 2 shows the configuration between the suction device 12 and the cartridge after the suction attachment 13 of the suction device 12 has come into contact with the measurement cell 8 and has pressed this so far down in the test chamber that the measurement cell 8 sits on a peripheral base 11 which is arranged on the inner wall of the test chamber 3. The measurement cell 8 is of cylindrical design and has a diameter smaller than the internal diameter of the test chamber 3. The upper, slightly bulged edge 16 of the measurement cell 8 lies on the inner wall of the test chamber 3. Arranged between the outside of the measurement cell 8 and the inner wall of the test chamber 3 there is a sealing element 15 which closes the test chamber off in an airtight manner from the outside atmosphere. When the measurement cell 8 moves down, the capillary tube 9 pierces the separating element 2 and comes into contact with the test fluid 4 in the fluid volume 7 or plunges into this test fluid 4. In this position of the measurement cell 8, an underpressure is generated in the measurement cell 8 by the suction device 12. The suction attachment 13 is equipped on the outside with an O-ring 14 which lies on the edge 16 of the measurement cell 8 and helps seal the measurement cell off from the outside atmosphere. By means of the underpressure applied to the measurement cell 8, test fluid 4 flows from the fluid volume 7 through the capillary tube 9 and into the measurement cell 8, and a fluid volume 10 of rising level forms. As test fluid 4 flows into the measurement cell 8, the fluid volume 7 decreases and the air cushion 6 expands, as a result of which an underpressure forms in the air space between the separating element 2 and the fluid volume 7. As soon as this underpressure is the same as the underpressure generated by the suction device 12 in the measurement cell 8, an equilibrium is achieved and, from this point in time onward, no more test fluid 4 flows into the measurement cell 8. The time span from when the test fluid 4 starts to flow, i.e. from when an underpressure of for example −40 mbar is generated in the measurement cell, to when the flow of the test fluid 4 stops, is measured in seconds and referred to as the closure time. The measurement principle underlying the closure time is thus based on an equilibrium between the underpressure in the air cushion above the fluid volume 7 and the underpressure in the measurement cell 8.

The test fluid 4 contains, for example, a mixture of glycerol and water, and its viscosity is set such that it corresponds to the viscosity of normal blood. The ratio of glycerol to water is 30:70 to 40:60, based on the total weight of the mixture of glycerol and water. In particular, the ratio of glycerol to water is 35:65 percent by weight, in each case based on the total weight of the mixture of glycerol and water.

The initial flow speed of the test fluid 4 is controlled by changing the length and the internal diameter of the capillary tube 9. The internal diameter of the capillary tube 9 lies in the range of 100 to 200 μm, in particular 150 to 210 μm. The length of the capillary tube 9 lies in the range of 15 to 30 mm. In a preferred embodiment, the internal diameter of the capillary tube is 200±10 μm, and the length of the capillary tube is 30 mm. The initial flow speed (IF) is 150 to 200 μl/min with a tolerance of about ±2.5 to 3%. The total volume of test fluid 4 is 300 to 400 μl, with a tolerance of ±5 to 7%. With the above-described configuration of the capillary tube 9 and the conditions for the initial flow speed and the total volume of the test fluid 4, a closure time of about 120 to 180 seconds is obtained, with a tolerance of ±5 seconds. The viscosity, the total volume and the initial flow speed of the test fluid 4 and the underpressure in the measurement cell 8 determine the closure time of the test fluid. When it is necessary, for some assays, to lengthen or shorten the closure time, the viscosity of the test fluid 4 can be increased or decreased by changing the ratio between glycerol and water. If the capillary tube 9 is shortened, the internal diameter of the capillary tube can also be reduced in order to maintain the initial flow speed. If the capillary tube is shortened while the internal diameter remains the same, the total volume of the test fluid must be reduced to be able to keep the flow speed constant. The greater the air volume, i.e. the initial air cushion 6 above the fluid volume 7, the longer the closure time of the test fluid. The initial flow speed, the total volume of test fluid, the air volume or air cushion 6 and the viscosity of the test fluid are chosen such that the standardized closure time of 120 to 180 seconds is maintained, which coincides with the closure time of normal blood. If it is found, in a measurement, that the closure time of the test fluid deviates from the standardized closure time, it can be assumed that the tested device for blood platelet diagnosis does not function satisfactorily. The material for the capillary tube 9 is preferably stainless steel, so that the defined narrow tolerance for the internal diameter of a relatively smooth inner surface can be maintained. The measurement cell 8 is expediently made of a plastic such as polypropylene or polyethylene terephthalate.

FIG. 3 shows a further embodiment of the cartridge in cross section. This embodiment differs from the embodiment shown in FIG. 2 only to the extent that the capillary tube 9 is integrated with the measurement cell 8 such that the capillary tube is connected integrally to the underside of the measurement cell 8 without extending into said measurement cell. The top face of the measurement cell 8 is closed except for a small opening 22. This opening 22 is connected to a suction attachment of the suction device 12. In the position shown in FIG. 3, the capillary tube 9 has likewise pierced the separating element 2 and is in contact with the test fluid 4 of the fluid volume 7. The suction device 12, which lies sealingly on the measurement cell 8 via the O-ring 14, has pushed the measurement cell 8 in the test chamber 3 so far down that the measurement cell sits on the base 11. In this embodiment of the measurement cell 8, the blocking ribs can be dispensed with, because the measurement cell is closed all round except for the small opening 22. As soon as the suction device 12 inside the measurement cell 8 generates an underpressure, the test fluid 4 rises through the capillary tube 9 into the measurement cell and there forms a rising fluid volume 10 until such time as the underpressure in the air cushion 6 above the fluid volume 7 is equal to the applied underpressure in the measurement cell 8.

The cartridge intended for one-off use is discarded together with the test fluid 4 in the measurement cell 8 at the end of the test. The cartridge shown in FIGS. 2 and 3 for one-off use is prepared for the test by the following steps. First, the test fluid 4 is introduced into the holding chamber 5, and the holding chamber 5 is then closed off in an airtight manner with the separating element 2. An air cushion 6 is present between the separating element 2 and the fluid volume 7. Next, a measurement cell 8 is introduced into the test chamber 3, and the test chamber is closed off in an airtight manner by means of a sealing element 15 which bears on the inner wall of the housing 1 of the cartridge and a partition wall between the test chamber 3 and the holding chamber 5. Thereafter, the top face of the housing 1 is closed off in an airtight manner with a closure element 19. The measurement cell 8 is located in a position near to the closure element 19, so that the capillary tube 9 connected to the measurement cell 8 is arranged with its lower end above the separating element 2, i.e. the separating element 2 is not pierced by the capillary tube 9. Next, and before inserting the cartridge into the device for blood platelet diagnosis, the closure element 19 over the test chamber 3 is removed. So far as the closure element 19 covers the holding chamber 5, it is maintained. In the next step, the capillary tube 9 connected to the measurement cell 8 inside the test chamber 3 is moved in the direction of the separating element 2, caused by the mechanical pressure exerted by the suction device 12 and applied to the measurement cell 8, as a result of which this is pushed downward until it sits on the base 11. In this movement, the capillary tube 9 pierces the separating element and comes into contact with the test fluid 4 of the fluid volume 7 or plunges into the test fluid. By means of the suction device 12, an underpressure is generated in the measurement cell 8 sufficient to ensure that test fluid flows through the capillary tube 9 into the measurement cell and a fluid volume 10 is built up therein. The time needed before the flow of test fluid into the measurement cell stops is measured. The application of the underpressure to the measurement cell marks the beginning of the time measurement. The closure time thus obtained is correlated with the time for the blood flow in a predetermined normal range of the device for blood platelet diagnosis.

Figure 4A:
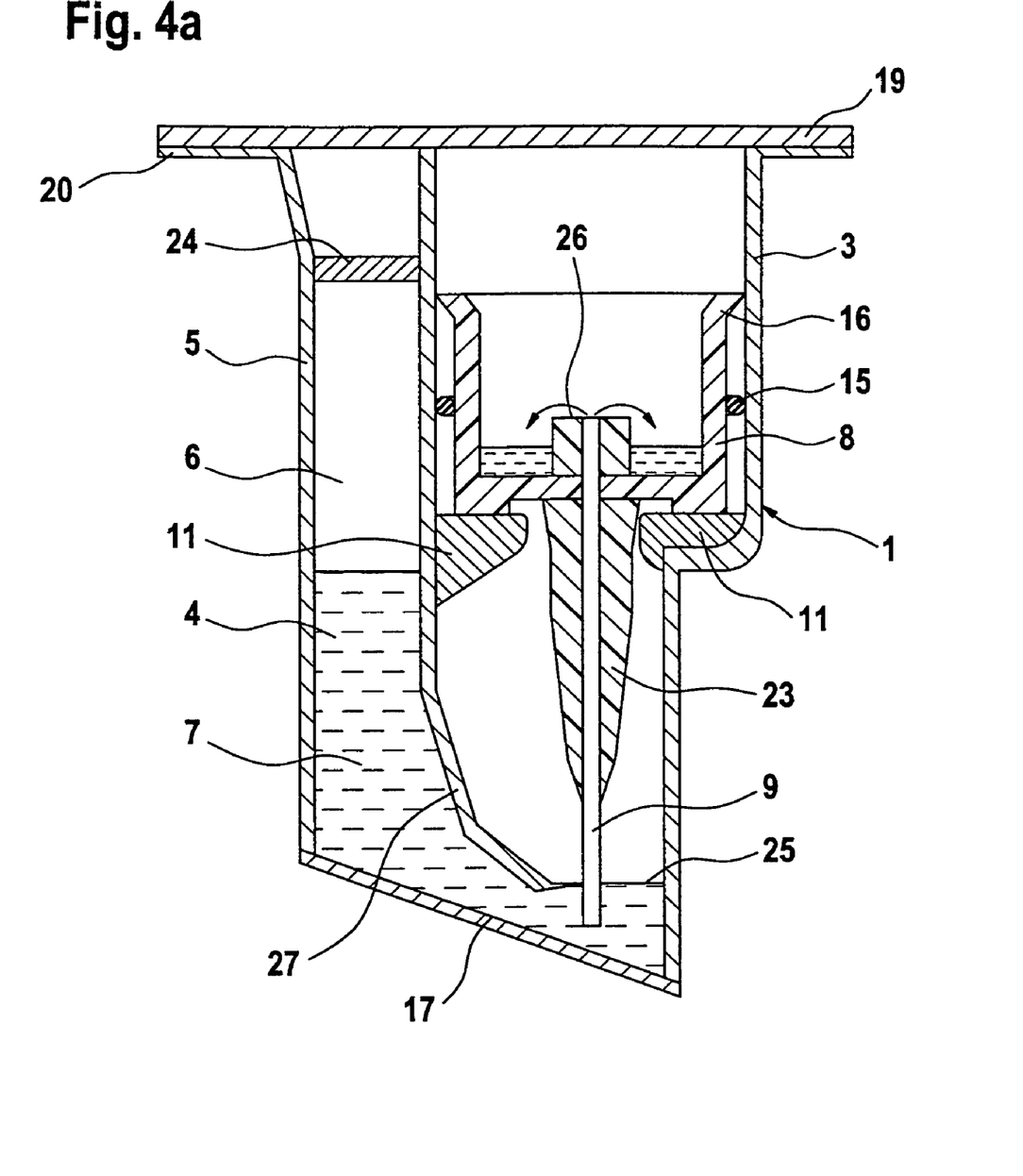
FIGS. 4a and 4b are cross sectional views of a third embodiment and a fourth embodiment of the cartridge along line I-I of FIG. 1.

FIG. 4a shows a third embodiment of the cartridge which is of a similar design to the embodiment according to FIG. 2.

The sealing element 15 is designed as an O-ring in this embodiment. The capillary tube is surrounded by a jacket 23 inside the holding chamber 5, and where the capillary tube 9 protrudes into the measurement cell 8, it is enclosed by a further jacket 26. Although this is not shown in the embodiments according to FIGS. 2 and 3, it is of course possible that in the first and second embodiments too the capillary tube 9 is or can in each case be surrounded by a jacket 23 and that the first embodiment additionally has a jacket 26. The capillary tube 9 passes through a separating element 25.

A wall 27 between the holding chamber 5 and the test chamber 3 reaches down almost to the inclined bottom 17 and is kinked or curved in the lower portion. The separating element 25 is located between the wall and a wall of the housing 1 and closes the holding chamber 5 off from the test chamber 3. The test fluid assumes a fluid volume 7 inside the holding chamber 5, the fluid volume filling about half the volume of the holding chamber 5. In the upper part of the holding chamber 5 there is a further separating element 24 which, after the test fluid 4 has been introduced, is inserted into the holding chamber 5 at a distance from the flange 20. The air cushion 6 is enclosed between this separating element 24 and the level of the test fluid 4. The other parts of the cartridge largely correspond to the first embodiment according to FIG. 2 and are labeled with the same reference numbers as in FIG. 2, so that they are not described again.

Figure 4B:
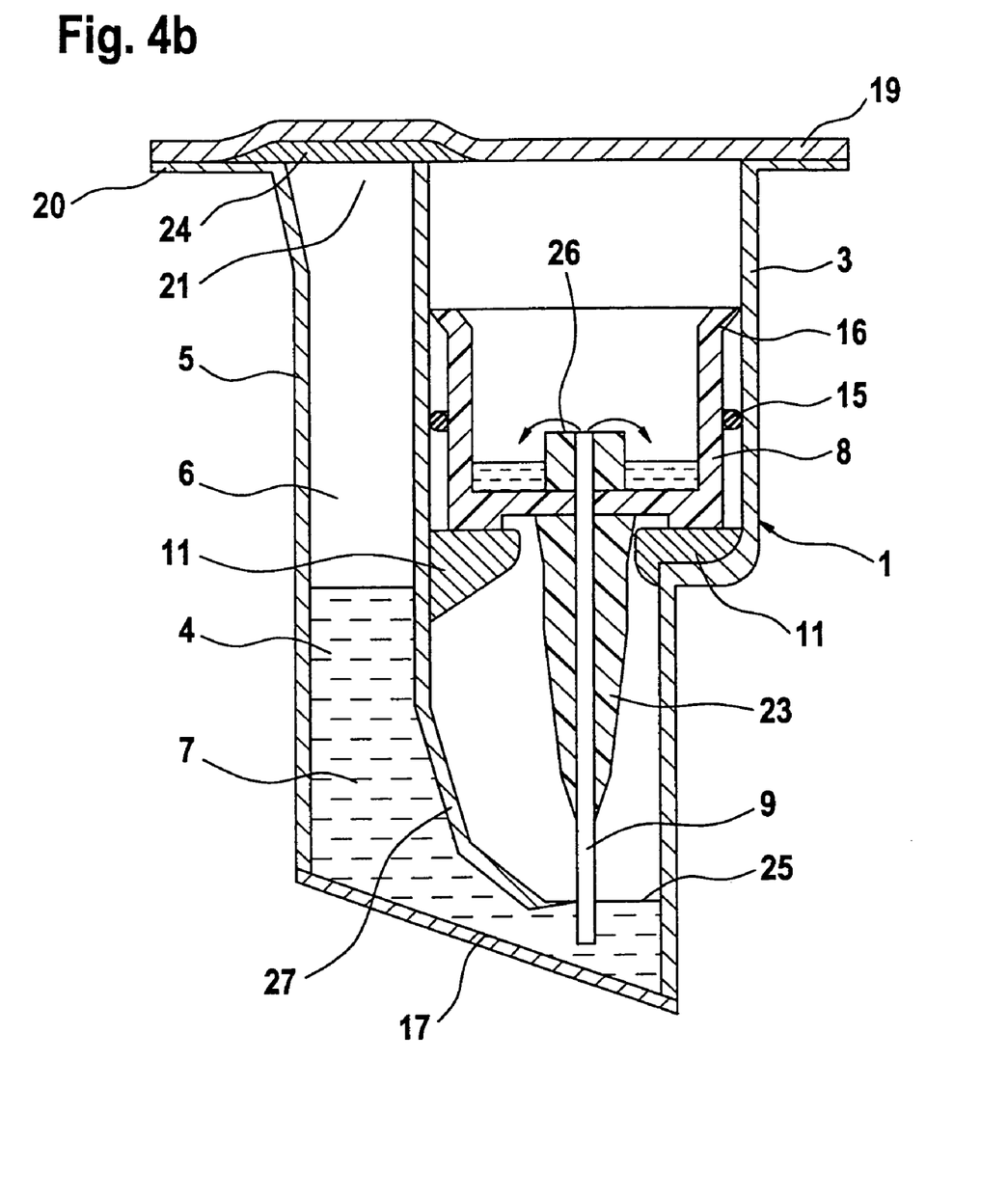

The fourth embodiment according to FIG. 4b is of a design similar to the third embodiment according to FIG. 4a, so that only the features different than the third embodiment are discussed below. In the fourth embodiment shown, the opening 21 of the holding chamber 5 is closed, after introduction of the test fluid, by the separating element 24 which lies on the flange 20. The upper closure element 19 of the cartridge spans the separating element 24 and forms a closure with the flange 20. After the closure element 19 has been pulled off from the flange 20, the holding chamber 5 is still closed in an airtight manner by the separating element 24. The closure element 19 is made of a self-adhesive film, for example. In the fourth embodiment, the air cushion 6 is larger than in the third embodiment because the separating element 24 closes flush with the opening 21 of the holding chamber and is not arranged inside the holding chamber, as is the case in the third embodiment.

The capillary tube 9 passes through the separating element 25.

The configuration between the suction device and the cartridge in the third and fourth embodiments is the same as has been described with reference to the first embodiment. For reasons of better clarity, the suction device is not shown in FIGS. 4a and 4b, but the underpressure exerted by the suction device allows the test fluid to flow through the capillary tube 9 into the measurement cell 8 and, there, the fluid volume 10 is built up until the underpressure in the air cushion 6 above the fluid volume 7 is equal to the applied underpressure in the measurement cell 8.

With longer or shorter closure times compared to the standardized closure time for normal blood or for other test samples, and by means of higher or lower initial flow speeds of the test fluid, it is possible to simulate not just normal but also abnormal blood states and thus monitor the function of devices for blood platelet diagnosis in respect of abnormal blood compositions. This can be achieved by selecting suitable test fluid, in particular its viscosity compared to the viscosity of the sample to be tested, in the cartridges according to the invention and in other embodiments according to the invention.

The invention claimed is:

1. A cartridge for monitoring the function of a device for testing blood platelet function, comprising:
   a housing including a holding chamber containing a fluid volume of a test fluid and further including a test chamber arranged laterally on the holding chamber;
   a measurement cell configured to be disposed in an upper portion of the test chamber;
   a capillary tube configured to connect the measurement cell to the fluid volume;
   a first separating element configured to separate the holding chamber from the test chamber; and
   a second separating element configured to seal the fluid volume of the test fluid and an air cushion disposed above the fluid volume within the holding chamber in a substantially airtight manner, without also sealing the test chamber.

2. The cartridge of claim 1, further comprising an upper closure element configured to seal the holding chamber and the test chamber.

3. The cartridge of claim 1, wherein the measurement cell is configured to be disposed on a peripheral base arranged on an inner wall of the test chamber.

4. The cartridge of claim 1, wherein the measurement cell has a substantially cylindrical shape.

5. The cartridge of claim 4, wherein the measurement cell has a diameter smaller than an inner diameter of the test chamber.

6. The cartridge of claim 1, further comprising a sealing element disposed between an exterior of the measurement cell and an inner wall of the test chamber,
   wherein the sealing element is configured to seal off the test chamber from the outside atmosphere in a substantially airtight manner.

7. The cartridge of claim 1, further comprising a suction device sealingly connected to the measurement cell.

8. The cartridge of claim 7, wherein the suction device is configured to generate an underpressure in the measurement cell.

9. The cartridge of claim 7, wherein the suction device includes a suction attachment having an O-ring.

10. The cartridge of claim 9, wherein the O-ring is disposed along an edge of the measurement cell.

11. The cartridge of claim 1, wherein an upper end of the capillary tube protrudes into the measurement cell.

12. The cartridge of claim 1, wherein the capillary tube passes through the first separating element such that a lower end of the tube may be positioned in the fluid volume.

13. The cartridge of claim 1, wherein a lower end of the capillary tube is configured to be disposed in the fluid volume.

14. The cartridge of claim 1, wherein the measurement cell includes only two openings, an opening in a top face of the measurement cell and an opening through which the capillary tube is connected to the measurement cell.

15. The cartridge of claim 1, wherein the capillary tube is integrally connected to the measurement cell.

16. The cartridge of claim 1, wherein the capillary tube does not protrude into the measurement cell.

17. The cartridge of claim 1, wherein the test fluid includes a mixture of glycerol and water.

18. The cartridge of claim 17, wherein an amount of glycerol present in the mixture is between about 30% and about 40% of a total weight of the mixture.

19. The cartridge of claim 17, wherein an amount of water present in the mixture is between about 60% and about 70% of a total weight of the mixture.

20. The cartridge of claim 17, wherein an amount of glycerol present in the mixture is about 35% of a total weight of the mixture and an amount of water present in the mixture is about 65% of a total weight of the mixture.

21. The cartridge of claim 1, wherein the test fluid includes at least one of water, oils, polyethylene glycol, and mixtures thereof.

22. The cartridge of claim 1, wherein the test fluid includes at least one of buffer substances, salts, antimicrobial substances, nucleic acid chains, carbohydrate chains, and proteins.

23. A method for monitoring the function of a device for testing blood platelet function, comprising:
   providing a cartridge including
      a housing having a holding chamber, which contains a fluid volume of a test fluid, and a test chamber arranged laterally on the holding chamber;
      a measurement cell configured to be disposed in an upper portion of the test chamber;
      a capillary tube configured to connect the measurement cell to the fluid volume;
      a first separating element configured to separate the holding chamber from the test chamber; and
      a second separating element configured to seal the fluid volume of the test fluid and an air cushion disposed above the fluid volume within the holding chamber in a substantially airtight manner, without also sealing the test chamber,
   moving the capillary tube within the test chamber in the direction of the first separating element;
   piercing the first separating element with the capillary tube such that the capillary tube comes into contact with the test fluid;
   generating a sufficient underpressure in the measurement cell such that the test fluid flows through the capillary tube and into the measurement cell;
   measuring a time period associated with when the test fluid stops flowing into the measurement cell;
   determining whether the measured time period deviates from a predetermined reference value, and
   determining, if the measured time period has been determined to deviate from the predetermined reference value, that the device for testing blood platelet function is not ready to be used.

24. The method of claim 23, further comprising choosing a test fluid having a viscosity substantially equal to a viscosity of a blood or a blood plasma in a normal state.

25. The method of claim 23, further comprising lengthening the measured time period by providing a test fluid having a viscosity greater than a viscosity of a blood or a blood plasma in a normal state.

26. The method of claim 23, further comprising shortening the measured time period by providing a test fluid having a viscosity less than a viscosity of a blood or a blood plasma in a normal state.

27. The method of claim 23, further comprising lengthening the measured time period by elongating the capillary tube.

28. The method of claim 23, further comprising lengthening the measured time period by reducing an internal diameter of the capillary tube.

29. The method of claim 23, wherein determining whether the measured time period deviates from a predetermined reference value includes determining whether the measured time period deviates from a predetermined reference value associated with normal blood.

30. A cartridge for monitoring the function of a device for testing blood platelet function, comprising:
   a housing including a holding chamber containing a fluid volume of a test fluid and further including a test chamber arranged laterally on the holding chamber;
   a measurement cell configured to be disposed in an upper portion of the test chamber;
   a capillary tube configured to provide contact between the measurement cell and the fluid volume; and
   a separating element configured to separate the fluid volume of the test fluid and an air cushion disposed above the fluid volume from the test chamber, and further configured to be pierced by the capillary tube.

31. The cartridge of claim 30, further comprising an upper closure element configured to seal the holding chamber and the test chamber.

32. The cartridge of claim 30, wherein the measurement cell is configured to be disposed on a peripheral base arranged on an inner wall of the test chamber.

33. The cartridge of claim 30, wherein the measurement cell has a substantially cylindrical shape.

34. The cartridge of claim 30, wherein the measurement cell has a diameter smaller than an inner diameter of the test chamber.

35. The cartridge of claim 30, further comprising a sealing element disposed between an exterior of the measurement cell and an inner wall of the test chamber,
   wherein the sealing element is configured to seal off the test chamber from the outside atmosphere in a substantially airtight manner.

36. The cartridge of claim 30, further comprising a suction device sealingly connected to the measurement cell.

37. The cartridge of claim 36, wherein the suction device is configured to generate an underpressure in the measurement cell.

38. The cartridge of claim 30, wherein an upper end of the capillary tube protrudes into the measurement cell.

39. The cartridge of claim 30, wherein the capillary tube passes through the separating element such that a lower end of the tube may be positioned in the fluid volume.

* * * * *